United States Patent
Moller et al.

(10) Patent No.: US 7,104,972 B2
(45) Date of Patent: Sep. 12, 2006

(54) INJECTION DEVICE WITH A DOSE SETTING LIMITER

(75) Inventors: Claus Schmidt Moller, Fredensborg (DK); Steffen Hansen, Hillerod (DK); Christian Sorensen, Hillerod (DK); Thomas Dedenroth Miller, Kobenhavn (DK)

(73) Assignee: Novo Nordisk A/S, Bagsvaerd (DK)

( * ) Notice: Subject to any disclaimer, the term of this patent is extended or adjusted under 35 U.S.C. 154(b) by 287 days.

(21) Appl. No.: 10/610,926

(22) Filed: Jul. 1, 2003

(65) Prior Publication Data

US 2004/0068236 A1 Apr. 8, 2004

Related U.S. Application Data

(60) Provisional application No. 60/401,546, filed on Aug. 6, 2002.

(30) Foreign Application Priority Data

Jul. 10, 2002 (DK) .......................... 2002 01085

(51) Int. Cl.
*A61M 5/00* (2006.01)

(52) U.S. Cl. .................. 604/207; 604/208; 604/211; 604/218; 604/223; 604/224; 604/232

(58) Field of Classification Search ............. 604/71–72, 604/181, 186–187, 207–211, 218, 220, 223–225, 604/228–229, 232, 246; 222/309, 390, 391
See application file for complete search history.

(56) References Cited

U.S. PATENT DOCUMENTS

| 5,271,527 A | | 12/1993 | Haber et al. .................. 222/43 |
| 5,304,152 A | * | 4/1994 | Sams ........................... 604/207 |
| 5,938,642 A | | 8/1999 | Burroughs et al. .......... 604/208 |
| 6,221,046 B1 | | 4/2001 | Burroughs et al. .......... 604/153 |

FOREIGN PATENT DOCUMENTS

| EP | 295075 | 12/1988 |
| EP | 554996 | 8/1993 |
| WO | 01/19434 | 3/2001 |

* cited by examiner

*Primary Examiner*—Nicholas D. Lucchesi
*Assistant Examiner*—Catherine S. Williams
(74) *Attorney, Agent, or Firm*—Marc A. Began, Esq.; Reza Green, Esq.; Richard W. Bork, Esq (57) ABSTRACT

An end-of-content arrangement for preventing a dose setting member of an injection device to be set to a dose larger that the medicament remaining in the injection device. The arrangement is particular suitable for injection devices operating with non-equistant dose volumes. The arrangement comprises an indentation provided on the housing or on the dose setting and injection member which indentation arrest a stop member when less than one dose unit is left in the cartridge. The stop member is coupled to the dose setting member such that the interaction between the indentation and the stop member prevents a dose larger that the remaining medication in being set.

3 Claims, 6 Drawing Sheets

INJECTION DEVICE WITH A DOSE SETTING LIMITER

CROSS REFERENCE TO RELATED APPLICATIONS

This application claims priority under 35 U.S.C. 119 of Danish application no. PA 2002 01085 filed Jul. 10, 2002 and U.S. provisional application No. 60/401,546 filed Aug. 6, 2002; the contents of both are fully incorporated herein by reference.

THE TECHNICAL FIELD OF THE INVENTION

The invention relates to an injection device of the kind having a housing accommodating a cartridge containing fluid medicine sufficient for a number of dosed injections, which doses are injected by advancing a piston rod forward inside the cartridge.

The invention especially relates to such an injection device having a dose setting limiter preventing a dose larger than the medicament remaining in the cartridge to be set.

DESCRIPTION OF RELATED ART

A prior art dose setting limiter is disclosed in WO 01.19434. This publication show in FIG. 2 a limiting mechanism which prevents the setting of a dose, which exceeds the amount of liquid left in a cartridge of an injection device. The injection device is the type where a dose is set by rotating a dose setting member relative to a driver and away from a fixed stop in the injection device. The dose setting member connects the driver such that the dose setting member can be rotated in one direction without rotating the driver. The dose is injected by rotating back the dose setting member which during the backwards rotation carries the driver with it. Rotating the driver causes the piston rod to move forward inside the cartridge and expel some of the liquid contained in the cartridge. The driver is provided with a track having a length which is related to the total amount of liquid in the cartridge and which track is engaged by a track follower operational coupled to the dose setting member to follow rotation of this dose setting member. Each time a dose is set and injected, the track follower moves further into the track. When the track follower reaches the end of the track the dose setting member cannot be rotated further, and a dose larger that the remaining liquid in the cartridge cannot be set.

The injection device disclosed in WO 01.19434 is particular suitable for injecting insulin. Insulin is usually produced with 100 international units (IU) of insulin pr. milliliter fluid, which are normally referred to as U100 insulin. The injection device shown in FIG. 1 of WO 01.19434 has a scale with 50 indications provided on a full circle. The full scale could however contain 60 indications like an ordinary egg timer, but the last ¹⁄₁₂ (=30 degrees) of the full circle bears no indications. One indication corresponds to one IU of insulin; it is therefore possible to set a maximum dose volume of 50 IU in one setting. All the dose indications on the scale are equidistant.

The length of the track of the driver determines how many IU it is possible for the user to set all together. The usual volume of the cartridge used in such a device is 3.0 ml. In terms of insulin this volume equals 300 IU when the cartridge is filled with a U100 insulin, the length of the track is therefore set to correspond to 300 IU. Since only dose volumes containing a full number of IU can be set and administered from the injection device, the last dose to be expelled before the track follower abuts the end of the track in the driver will always be a full number of International Units (IU) and at least one full IU.

DESCRIPTION OF THE INVENTION

This prior art injection device has proven itself very attractive to people suffering from diabetes. The end of content feature of the device is however not suitable if the device is operating with non-equidistant dose volumes.

Prior to performing an injection it is customary to perform a so called air shot in order to empty the cartridge for any surplus of air. This is done by setting up a small dose of medicament, positioning the injection device in an upright position and injecting the set dose into the air. This procedure is being continued until medicament is expelled from the needle.

For some medicaments the dose volumes to be injected are fairly large, which is no problem with the injection device described. It is however beneficial to provide injection devices with large incremental dose settings with an additional air shot dose setting provided between the zero setting and the first setting. Now when introducing such non-equidistant dose setting, the prior art end of content feature is no longer suitable.

If e.g. one large incremental dose setting corresponds to 0.05 ml fluid medicament (i.e. 5 IU if the medicament is a U100 insulin), a total of 60 doses are available in a standard 3 ml. cartridge. The prior art end of content feature will then allow 60 full doses to be set. If however an air shot dose setting is provided which e.g. equals 0.02 ml fluid medicament (i.e. 2 IU U100 insulin) the user could end in a situation where the prior art end of content feature will stop the setting of a dose when only a part of a large incremental dose has been set with the result that the last dose is not a full dose.

If e.g. 55 dose units of 0.05 ml (i.e. 2.75 ml) has been distributed and 11 air shots of 0.02 ml (i.e. 0.22 ml) has been performed, the remaining usable volume in the cartridge is 0.03 ml due to the prior art track having a length corresponding to 3.0 ml. The last dose the user can set in this case is therefore 0.03 ml, which is not a full dose (one full dose=0.05 ml.).

The present invention aims to solve this problem by providing a trustworthy synchronized end of content feature which will ensure that the last dose will always be a full dose also when the device is operating with non-equidistant dose volumes.

The general concept of the present invention is to synchronize the end of content feature with the dose setting mechanism of an injection device operating with large non-equistant dose volumes.

This is achieved by providing an arrangement comprising a stop member which is operational coupled to the dose setting member and at least one barb which is provided on either the dose setting and injection mechanism or on the housing. When the number of summarized doses set by dose setting member reached a level where there are less than one full dose left in the cartridge, the stop member will be in a position where it engages one of the barbs thereby preventing a dose larger than the remaining in the cartridge of being set by the user.

The principle of having a driver surrounded by a coupling ring and the stop member connected to the coupling ring makes this solution especially suitable for the Innolet® device known from WO 01.83008.

The stop member is provided as an appendix on an arm connected to the coupling ring, it is ensured that the stop member can extend beyond the peripheral boundaries of the driver and interact with the dose volume indentations provided either on the housing or on the dose setting and injecting mechanism.

The arm is provided with a cam being guided in a spiral track in the driver, it is ensured that the movement of arm and thereby the appendix is synchronized with the rotation of the driver.

It is specified that the stop member is guided into abutment with one of the indentations when there is less than one unit of medicament left in the cartridge. The end of content feature is henceforth a result of the length of the track and the position of the indentations. When the distance between the indentations equals the size of the doses the user can select, it is ensured that the appendix will pass over an indentation when there are more than one full dose left in the cartridge but be arrested by an indentation when there is less than one full dose of medicine left in cartridge.

BRIEF DESCRIPTION OF THE DRAWINGS

The invention will be explained more fully below in connection with a preferred embodiment and with reference to the drawings in which.

The figures are schematic and simplified for clarity, and they just show details, which are essential to the understanding of the invention, while other details are left out. Throughout, the same reference numerals are used for identical or corresponding parts.

DETAILED DESCRIPTION OF EMBODIMENT

Initially it may be convenient to define that, the term "distal end" is meant to refer to the end of the injection device carrying the injection needle to be inserted into the patient, whereas the term "proximal end" is meant to refer to the opposite end pointing away from the patients body when injecting the medicament.

Figure 1:
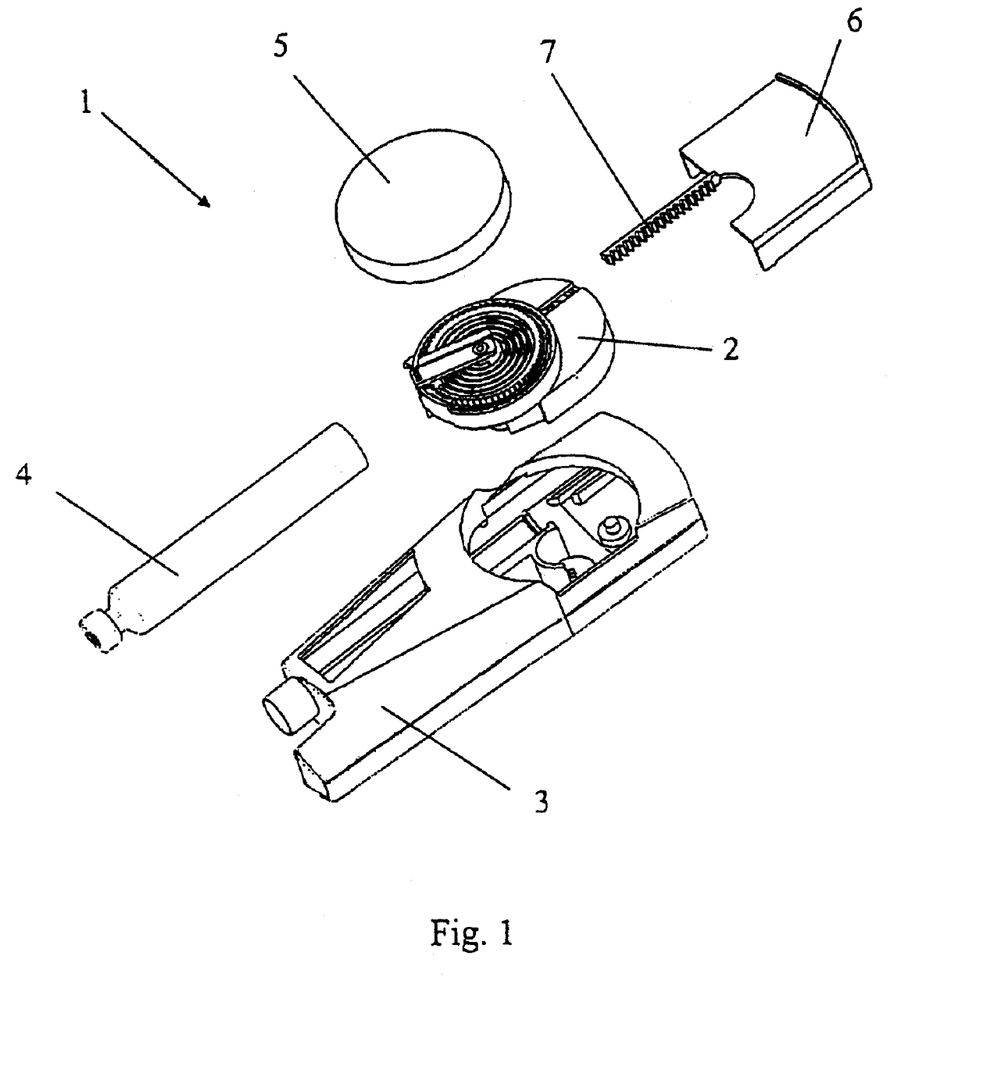
FIG. 1 Shows an exploded view of an injection device.

The injection device 1 disclosed in FIG. 1 comprises a dose and injection mechanism 2 insertable into a housing 3. Also insertable into the housing 3 is the cartridge 4 containing the fluid medicament. A dose setting button 5 and an injection button 6 is connected to the dose and injecting mechanism 2. The injection button 6 is provided with a toothed rack 7, which operates the dose setting and injection mechanism 2 to deliver a dose.

Figure 2:
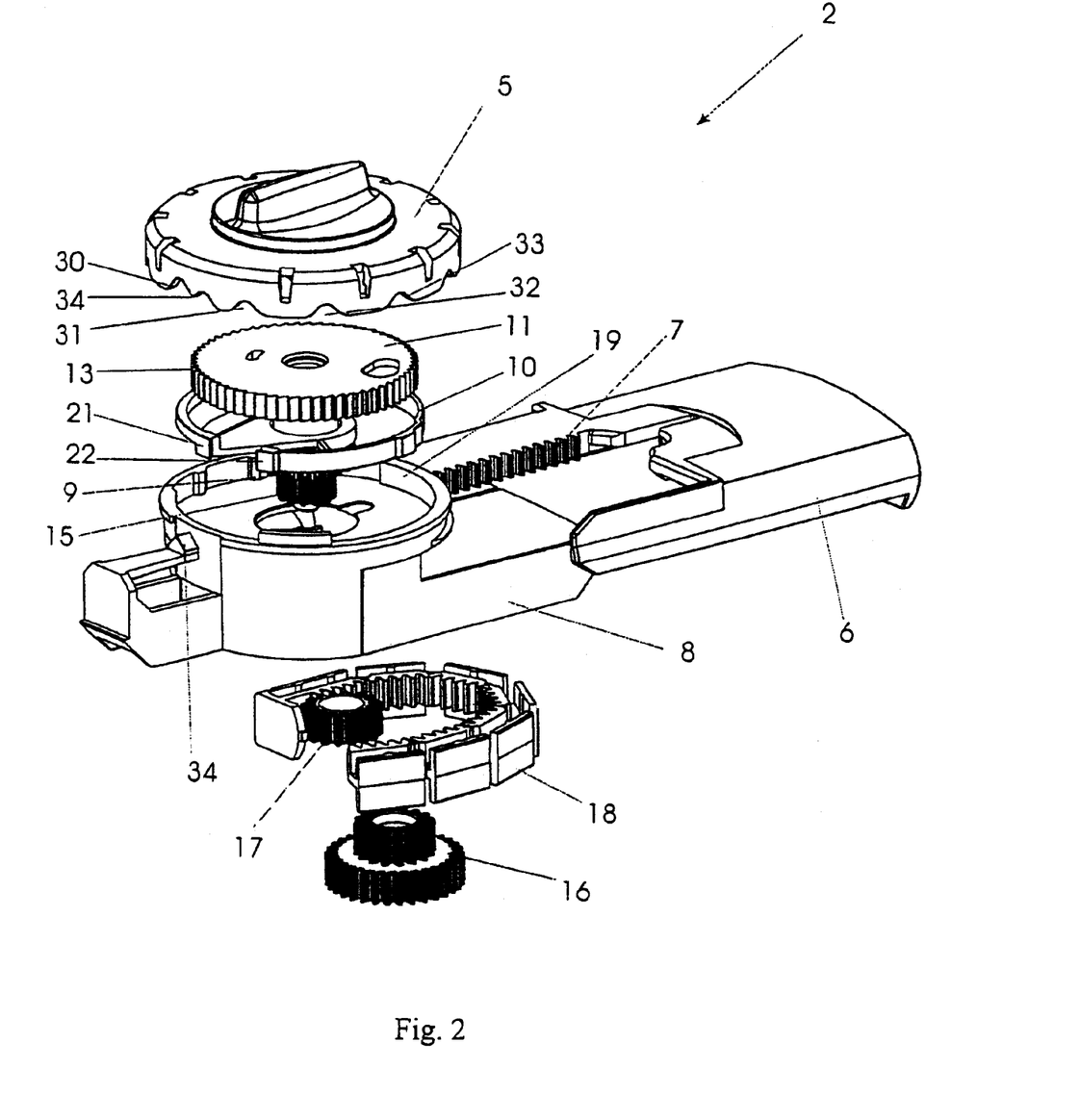
FIG. 2 Shows an exploded view of the dose setting and injection mechanism according to the invention.

FIG. 2 discloses the dose setting and injecting mechanism 2 according to the invention. The toothed rack 7 of the injection button 6 engages the coupling ring wheel 9 through a slot in the rod guiding part 8. The coupling ring wheel 9 is integral with the coupling ring 10, which coupling ring 10 engages the driver 11. This engagement is obtained by one or more barbs 12 (seen in FIG. 3) located on the inside surface of the coupling ring 10 engaging the outer toothing 13 of the driver 11.

An arm or protrusion 14 provided on an inside surface 19 of the rod guiding part 8 engages the outer toothing 13 of the driver 11 and prevents the driver 11 from rotation in one direction. The direction in which the driver 11 can move freely is the direction in which the piston rod 9 is moved forward inside the cartridge 4.

On the flipside of the rod guiding part 8, the toothed axis 15 of the driver 11 engages the second gear wheel 16. The second gear wheel 16 engages the first gear wheel 17 which transmits the rotational movement to the piston rod 18.

Figure 3:
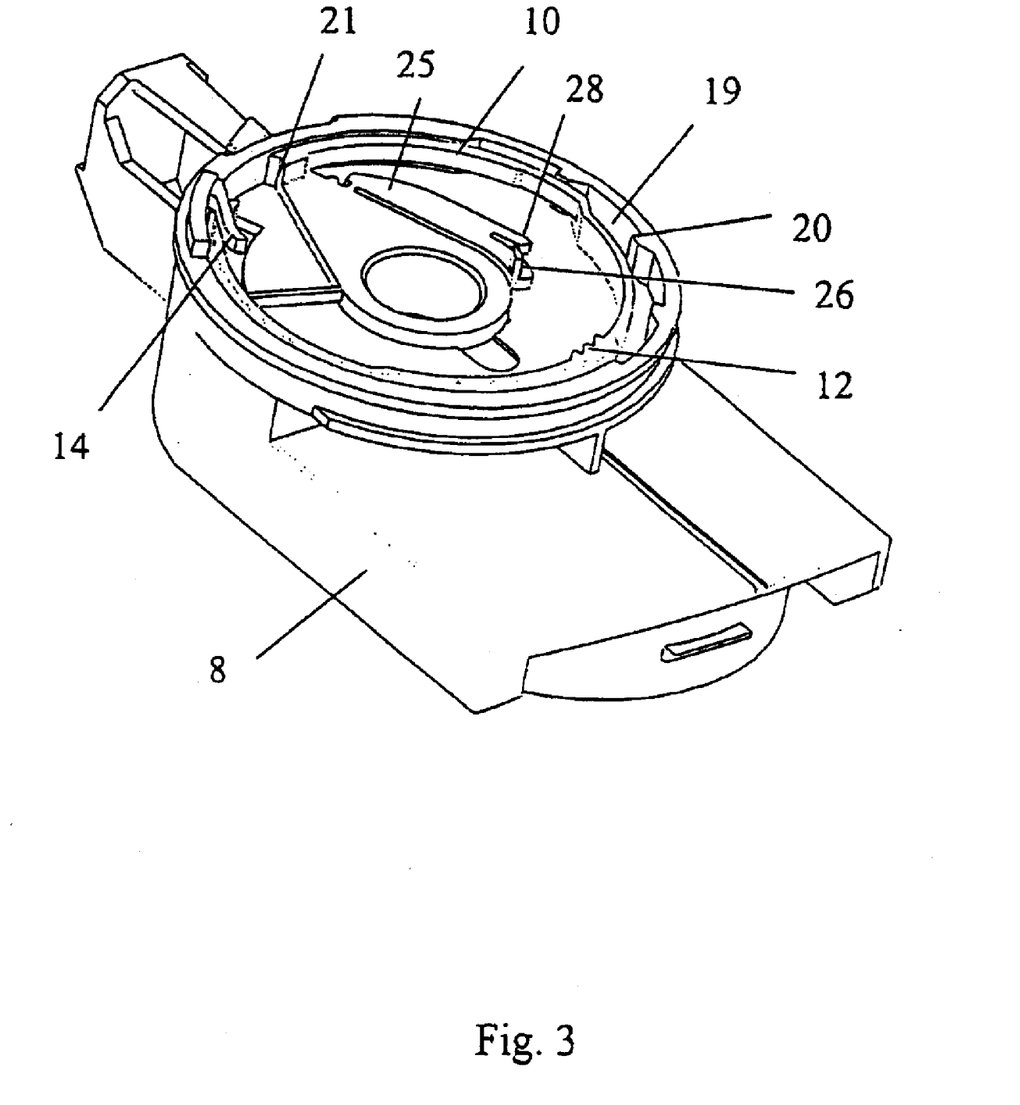
FIG. 3 Shows a schematically top view of the dose setting and injection mechanism.
Figure 4:
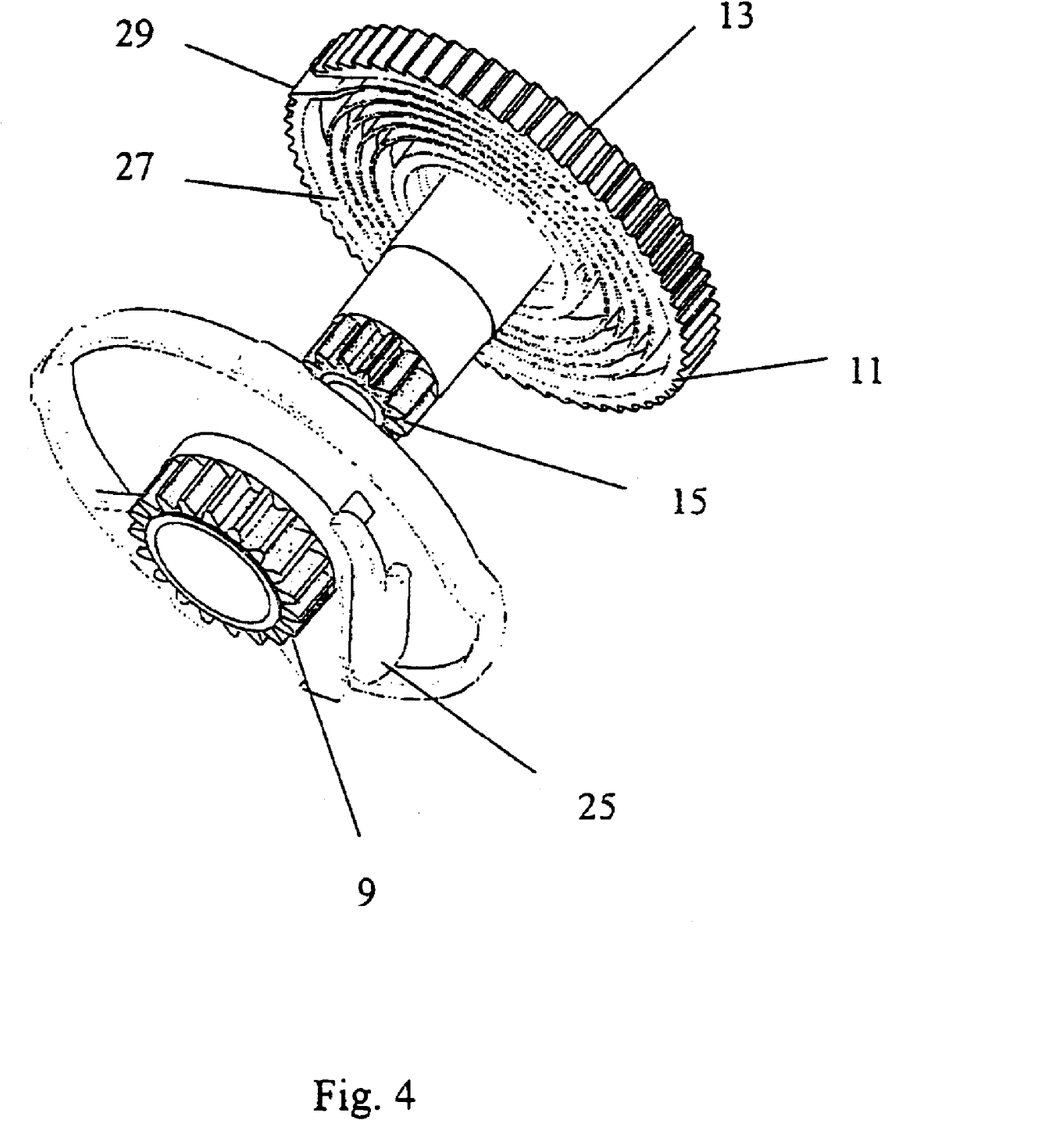
FIG. 4 Shows an exploded view of the driver and the coupling ring of the dose setting and injection mechanism.
Figure 5:
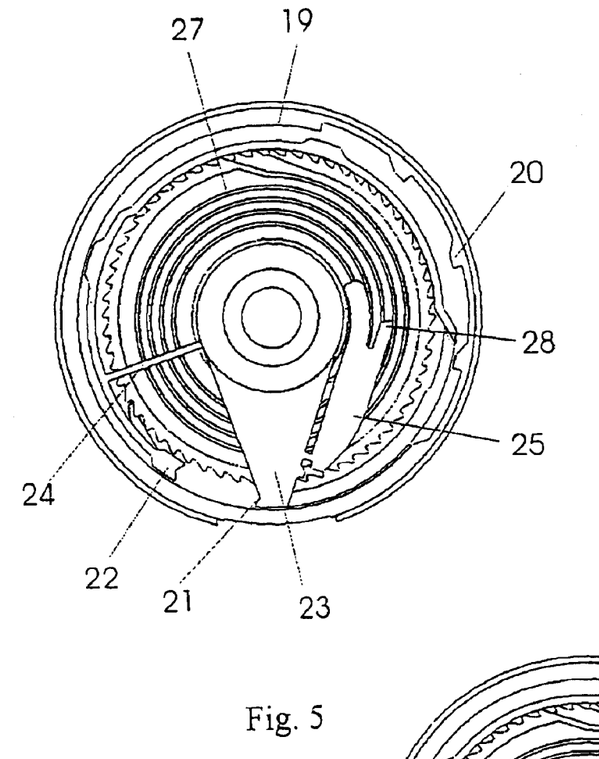
FIG. 5 Shows a cross sectional view through the dose setting and injection mechanism according to the invention FIG. 6 Shows a cross sectional view through the dose setting and injection mechanism according to the invention with the arm in the extended position.
Figure 6:
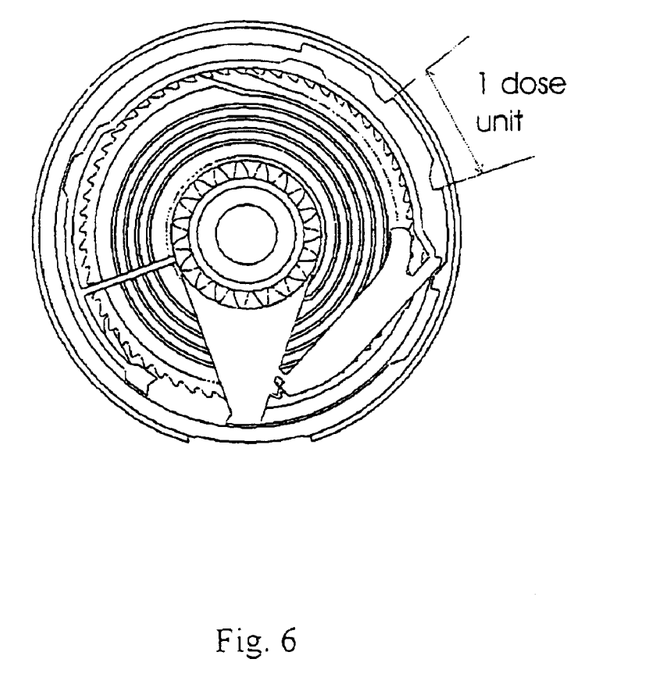

As shown in FIG. 3, the inside surface 19 of the rod guiding part 8 is left as a smooth surface. The smooth inside surface 19 is however provided with a number of indentations 20, the use of which will be explained later.

When operating the injection device 1, the dose to be delivered is first set by turning the dose setting button 5 in the clockwise direction. The backside of the dose setting button 5 is provided with a not shown notch which interfaces the coupling ring 10 such that the coupling ring 10 moves with the dose setting button 5. The not shown notch fills the opening in the coupling ring 10 between the first bulging end 21 and the second bulging end 22. During this rotation, the driver 11 is prevented from rotation by the protrusion 14 and the barbs 12 rides over the outer toothing 13 on the driver 11. Since the coupling ring wheel 9 interacts with the toothed rack 7 of the injection button 6, this injection button is lifted away from the housing 3 when the dose setting button 5 is rotated.

The dose setting button 5 has a number of equidistant dose setting indentations 30, 31, 32, 33 which clicks on the clicking protrusion 34. The first indentation 30 is the zero setting whereas the second dose setting indentation 31 equals one full dose, the third dose setting indentation 32 represents two full doses. The whole peripheral area of the circular dose setting button 5 can be equipped with similar indentations. When these doses are large, it is beneficial to provide a separate air shot indentation 34 representing a somewhat smaller dose.

When delivering the set dose, the injection button 6 is pressed back home to its original position. The toothed rack 7 of the injection button 6 forces the coupling ring 10 to rotate thereby translating the longitudinal movement of the injection button 7 to a rotational movement of the coupling ring 10. The barbs 12 on the inside surface of the coupling ring 10 interacts with the outer toothing 13 of the driver 11 hence rotating the driver 11 in the anti-clockwise direction. The rotation of the driver 11 is transmitted through the second gear wheel 16 to the first gear wheel 17, which first gear wheel 17 engages the piston rod 18. Rotation of the first gearwheel 17 causes the piston rod 18 to move forward inside the cartridge 4 thereby expelling the set dose of medicine through a not shown conduit connected to the distal end of the cartridge 4.

If a set dose is regretted, the dose setting member 5 is simply rotated in the anti-clockwise direction. The coupling ring 10 is connected to the coupling ring wheel 9 through a solid member 23 and a flexible member 24. Since rotation of the dose setting member 5 in the anti-clockwise direction causes the force to be applied onto the flexible member 24, the coupling ring 10 will expand outwardly allowing the barbs 12 to slide over the outer toothing 13 of the driver 11.

Hence the driver 11 is not affected by this backward rotation of the coupling ring 10.

The inside of the coupling ring 10 is further provided with an arm 25 which is flexible hinged to the coupling ring 10 as disclosed in FIGS. 3-6. The arm 25 is equipped with a cam 26 engaging a spiral shaped track 27 provided on the driver 11. When the dose setting member 5 and the coupling ring 10 is rotated in the clockwise direction during the setting of a dose, the cam 26 on the arm 25 is moved along the track 27 in an outward direction whereas the cam 26 during injection due to the concomitant rotation of the coupling ring 10 and the driver 11 remains in its position in the track 27 obtained during the dose setting. This way the position of the cam 26 reflects the total amount of medicine administered.

The arm 25 is provided with an appendix 28 which will be outside the periphery of the driver 11 when the cam 26 is in located in the outer winding of the track 27.

The inside surface 19 of the rod guiding part 8 is provided with a number of indentations 20 each having a steep front. These indentations 20 can be applied along the entire surface or restricted to the area which is used for setting up a dose for the specific injection device.

The circular distance between the indentations 20 equals the size of the doses which the user can set using the dose setting button i.e. the distance between the barbs 20 equals the distance between the dose setting indentations 30, 31, 32, 33 on the dose setting member 5 such that the end of content feature is synchronized with the dose setting scale. In this way the appendix 28 will abut an indentation 20 when there is less than one unit of medicine in the cartridge 4, while the appendix 28 will be able to pass over the indentation 20 when there is one or more units left in the cartridge 4. The length of the spiral track 27 is synchronized with the content in the cartridge 4 such that the cam 26 is guided out through the track opening 29 when the cartridge 4 is almost empty. When the cam 26 is located in the track opening 29, the appendix 28 will be outside the boundaries of the driver 11 and ready to abut the next indentation 20. The result of this is that the last dose the user can set on the injection device 1 will always be a full dose.

Figure 7:
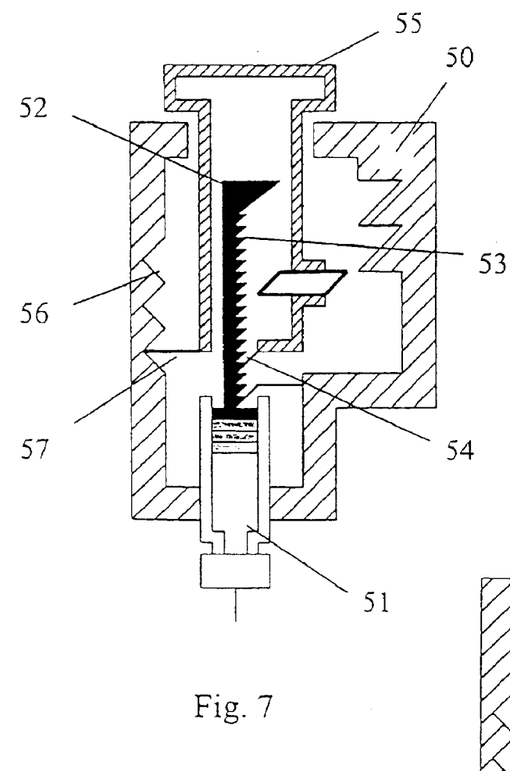
FIG. 7 Shows an embodiment of the invention with a full cartridge.
Figure 8:
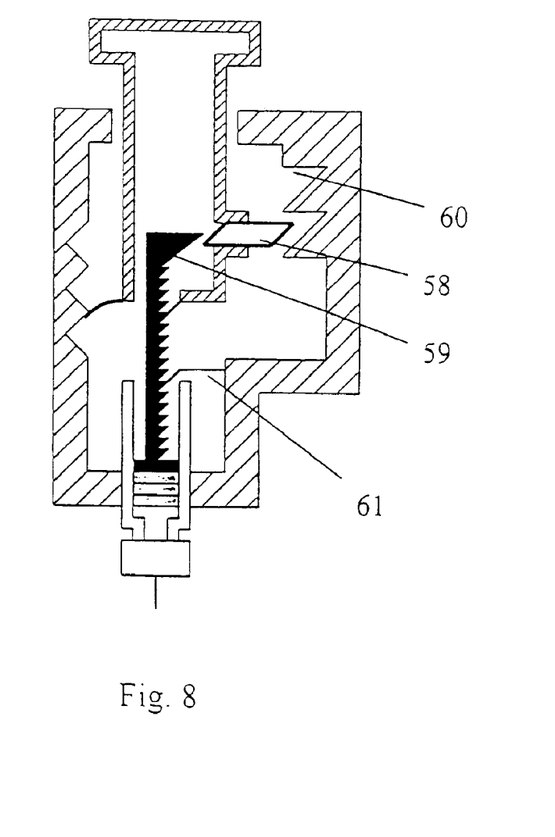
FIG. 8 Shows an embodiment of the invention with an empty cartridge.

FIGS. 7 and 8 discloses an embodiment of the invention comprising a housing 50 accommodating a cartridge 51 containing a fluid medicament. The piston rod 52 comprises a rigid elongated toothed rack 53.

The dose setting and injecting mechanism comprises the toothed rack 53 and a protrusion 54 provided on the dose setting button 55. The engagement between the toothed rack 53 and the protrusion 54 is such that the protrusion 54 slides over the toothed rack 53 when the dose setting button 55 is pulled away from the housing 50 and that the toothed rack 53 and thereby the piston rod 52 moves forward together with the dose setting button 55 when a dose is administered.

The dose setting button 55 is used for setting up a dose by pulling the button 55 away from the housing 50, but acts as an injection button when it is pressed towards the housing 50.

A number of dose setting barbs 56 are provided in the wall of the housing 50, which indentations is engages by a ratchet 57 operational connected to the dose setting button 55. The length between the indentations 56 expresses the size of the doses the user can select.

A stop member 58 is connected horizontally movable to the dose setting member 55. At the proximal end of the piston rod 52 a sloping surface 59 is provided against which sloping surface 59 the stop member 58 is pressed when the piston rod 52 is moved to the distal end of the cartridge 51.

A number of indentations 60 is provided in the housing 50 with a distance that equals the distance between the dose setting barbs 56. Once the cartridge 51 is almost empty as shown in FIG. 8 and the piston rod 52 is moved to the distal end of the cartridge 51, the stop member 58 will be pushed in the horizontal direction by the sloping surface 59. This will cause the stop member 58 to engage one of the indentations 60 and thereby prevent the dose setting member 55 from being moved further in the proximal direction.

Due to the relation between the distance between the indentations 60 and the distance between the dose setting barbs 56, the stop member 58 will slide over an indentations 60 if there is more than one dose unit of medicine in the cartridge 51, but be arrested by an indentations 60 if there is less than one dose unit of medicine left in cartridge 51.

The toothed rack 53 is prevented from moving backward relative to the housing by a one-way protrusion 61 engaging the toothed rack 53.

Some preferred embodiments have been shown in the foregoing, but it should be stressed that the invention is not limited to these, but may be embodied in other ways within the subject matter defined in the following claims.

| LISTING OF PARTS | |
|---|---|
| 1 | Injection Device |
| 2 | Dose Setting and Injection Mechanism |
| 3 | Housing |
| 4 | Cartridge |
| 5 | Dose Setting Button |
| 6 | Injection Button |
| 7 | Toothed Rack |
| 8 | Rod Guiding Part |
| 9 | Coupling Ring Wheel |
| 10 | Coupling Ring |
| 11 | Driver |
| 12 | Barbs |
| 13 | Outer Toothing |
| 14 | Protrusion |
| 15 | Toothed Axis |
| 16 | Second Gear Wheel |
| 17 | First Gear Wheel |
| 18 | Piston Rod |
| 19 | Inside Surface |
| 20 | Indentations |
| 21 | First Bulging end |
| 22 | Second Bulging end |
| 23 | Solid Member |
| 24 | Flexible Member |
| 25 | Arm |
| 26 | Cam |
| 27 | Spiral Track |
| 28 | Appendix |
| 29 | Track Opening |
| 30 | First Dose Setting Indentation (= zero setting) |
| 31 | Second Dose Setting Indentation (= one full dose) |
| 32 | Third Dose Setting Indentation (= two full doses) |
| 33 | Fourth Indentation |
| 34 | Air Shot Indentation |
| 50 | Housing |
| 51 | Cartridge |
| 52 | Piston Rod |
| 53 | Toothed Rack |
| 54 | Protrusion |
| 55 | Dose Setting Button |
| 56 | Dose Setting Barbs |
| 57 | Ratchet |
| 58 | Stop Member |
| 59 | Sloping Surface |
| 60 | Indentations |
| 61 | One-way Protrusion |

What is claimed is:

1. An injection device having a housing accommodating a cartridge containing medicine sufficient for a number of dosed injections, whereby doses are injected by advancing a piston rod forward inside the cartridge, the injection device comprising:

a dose setting and injection mechanism, a dose setting member operational coupled to the dose setting and injection mechanism for setting up a dose to be injected, an injection button operational coupled to the dose setting and injecting mechanism and by which the dose setting and injection mechanism can be activated for advancing the piston rod forward in order to press out the set dose through a conduit connected to the cartridge, and an arrangement for preventing the dose setting member to be set to a dose larger than the medicament remaining in the cartridge, wherein, said arrangement comprises a stop member operational coupled to the dose setting member engaging one of a plurality of indentations provided on the dose setting and injection mechanism or on the housing when less than one dose unit is left in the cartridge thereby preventing a dose larger than the medicament remaining in the cartridge of being set, wherein, the stop member is connected to the dose setting member through a coupling ring surrounding a driver, wherein, the stop member is provided as an appendix on an arm connected to the coupling ring, wherein, the arm is provided with a cam being guided in a spiral track in the driver.

2. An injection device according to claim 1, wherein the stop member is guided into abutment with the indentation when there is less than one unit of medicament left in the cartridge.

3. An injection device according to claim 1, wherein, the circular distance between two following indentations equals one selectable dose unit.

* * * * *